United States Patent [19]

Schwan

[11] 4,028,359
[45] June 7, 1977

[54] 2-DIETHOXYETHYL(DIMETHYL)(2-(2,4-DIPHENYL-5-PYRIMIDYL)-2-OXOETHYL-)AMMONIUM BROMIDE

[75] Inventor: Thomas J. Schwan, Norwich, N.Y.

[73] Assignee: Morton-Norwich Products, Inc., Norwich, N.Y.

[22] Filed: May 3, 1976

[21] Appl. No.: 682,397

[52] U.S. Cl. .......................... 260/256.4 R; 424/251
[51] Int. Cl.² ....................................... C07D 239/24
[58] Field of Search ............................ 260/256.4 R

[56] References Cited

UNITED STATES PATENTS

| | | | |
|---|---|---|---|
| 3,920,651 | 11/1975 | Ecsery et al. | 260/256.4 R |
| 3,944,581 | 3/1976 | Schwan | 260/256.4 R |
| 3,969,355 | 7/1976 | Schwan | 260/256.4 R |

OTHER PUBLICATIONS

Jamison, "Chemical Abstracts", col. 86957f, vol. 68, 1968.
Lucas, "*Organic Chemistry,*" Sec. Ed., 1953, American Book Co., New York, pp. 351–352.

*Primary Examiner*—Donald G. Daus
*Assistant Examiner*—James H. Turnipseed
*Attorney, Agent, or Firm*—Anthony J. Franze

[57] ABSTRACT

The title compound is a useful anthelmintic agent.

1 Claim, No Drawings

2-DIETHOXYETHYL(DIMETHYL)(2-(2,4-DIPHENYL-5-PYRIMIDYL)-2-OXOETHYL)AMMONIUM BROMIDE

This invention relates to chemical compounds. In particular it is concerned with a compound of the formula:

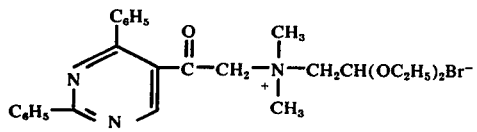

It is useful as an anthelmintic agent. When administered per os by gavage in an aqueous methyl cellulose suspension at a dose of about 100 mg/kg to mice harboring the pinworm syphacia obvelata, a 79% reduction of pinworm population is secured.

The method currently preferred for the preparation of the compound of this invention is briefly described as follows:

A. 2,4-Diphenyl-5-pyrimidyl bromomethyl ketone

An 86 g (0.31 mole) portion of 2,4-diphenyl-5-pyrimidyl methyl ketone in 1.1 l. of dioxane was treated with 136 g (0.61 mole) of cupric bromide using rapid stirring. The reaction mixture was stirred for 15 hrs at ambient temperature, refluxed for 3 hrs, cooled, stirred for 2 additional hrs and filtered. The off-white solid was washed with two 300 ml portions of chloroform. The filtrate and washings were combined and concentrated to dryness under reduced pressure to give a gray crystalline solid.

The crude product was recrystallized from 2 l. of absolute ethanol. The off-white solid was washed with 200 ml of absolute ethanol and air dried, m.p. 131°–133°. Yield: 57 g (52%).

Anal. Calcd. for $C_{18}H_{13}BrN_2O$: C, 61.20; H, 3.31; N, 7.93. Found: C, 61.68; H, 3.68; N, 7.95.

B. 2-Diethoxy(dimethyl)[2-(2,4-diphenyl-5-pyrimidyl)-2-oxoethyl]ammonium bromide A 27.5 g (0.078 mole) portion of A in 300 ml benzene was treated with 12.6 (0.078 mole) of dimethylaminoacetaldehyde diethylacetal. The reaction mixture was refluxed for 5 hrs. The slurry was stirred overnight at room temperature and filtered. The white solid was washed with 150 ml of benzene and air dried, m.p. 98°–108°. Yield: 38 g (95%).

A 36 g portion of the crude product was recrystallized from 150 ml of acetone and air dried, m.p. 149°–151°. Yield: 28 g (70%).

An analytical sample, m.p. 152°–154°, was recrystallized from acetone at 50 ml/g.

Anal. Calcd. for $C_{26}H_{32}BrN_3O_3$: C, 60.70; H, 6.27; N, 8.17. Found: C, 60.92; H, 6.43; N, 8.14.

What is claimed is:

1. 2-Diethoxyethyl(dimethyl)[2-(2,4-diphenyl-5-pyrimidyl)-2-oxoethyl]ammonium bromide.

* * * * *